United States Patent
Bolz

(10) Patent No.: US 7,473,340 B2
(45) Date of Patent: Jan. 6, 2009

(54) CIRCUIT CONFIGURATION FOR OPERATING A LINEAR EXHAUST-GAS PROBE

(75) Inventor: Stephan Bolz, Pfatter (DE)

(73) Assignee: Siemens Aktiengesellschaft, Munich (DE)

(*) Notice: Subject to any disclaimer, the term of this patent is extended or adjusted under 35 U.S.C. 154(b) by 811 days.

(21) Appl. No.: 11/088,515

(22) Filed: Mar. 24, 2005

(65) Prior Publication Data

US 2005/0189221 A1  Sep. 1, 2005

Related U.S. Application Data

(63) Continuation of application No. PCT/DE2003/002822, filed on Aug. 22, 2003.

(30) Foreign Application Priority Data

Sep. 24, 2002 (DE) .................. 102 44 466

(51) Int. Cl.
*G01N 27/409* (2006.01)
*G01N 27/41* (2006.01)
(52) U.S. Cl. .............. 204/406; 204/425; 73/23.32
(58) Field of Classification Search .......... 204/406, 204/424, 425; 205/784.5, 785; 73/23.32
See application file for complete search history.

(56) References Cited

U.S. PATENT DOCUMENTS

| 4,665,874 A | 5/1987 | Kawanabe et al. |
| 4,698,209 A | 10/1987 | Hashimoto et al. |
| 4,732,127 A | 3/1988 | Kawanabe et al. |
| 5,047,137 A | 9/1991 | Yamada et al. |
| 5,340,462 A * | 8/1994 | Suzuki .................. 204/425 |
| 2004/0007045 A1 | 1/2004 | Bolz |

FOREIGN PATENT DOCUMENTS

| DE | 101 01 755 C1 * | 7/2002 |
| JP | 61294357 A | 12/1986 |
| JP | 62081559 A | 4/1987 |
| JP | 2002257772 A | 9/2002 |

OTHER PUBLICATIONS

Patent Abstract for JP 63-279160, Nov. 1988.*
Japanese Office Action dated Aug. 13, 2008.

* cited by examiner

*Primary Examiner*—Kaj K Olsen
(74) *Attorney, Agent, or Firm*—Laurence A. Greenberg; Werner H. Stemer; Ralph E. Locher

(57) ABSTRACT

A linear exhaust-gas probe has a measuring cell for measuring a gas concentration in a measuring chamber by determining a measuring-cell voltage, and a pump cell for pumping gas by way of a pump current. A circuit configuration for operating the prove has a comparator circuit for comparing the measuring-cell voltage with a measuring-cell setpoint voltage and for providing a corresponding analog deviation signal. A pump current source provides the pump current. The source is controlled by the deviation signal using a control circuit for the approximation of the measuring cell voltage to the measuring cell setpoint voltage. In order to reliably limit the pump voltage with no significant detrimental effect on the operation, the circuit configuration further has a second comparator circuit for comparing the pump voltage with a predefined threshold voltage and for providing a corresponding binary switching signal; and a counter coupling path between the output of the pump current source and the control circuit. The path is enabled when the voltage threshold is crossed.

6 Claims, 7 Drawing Sheets

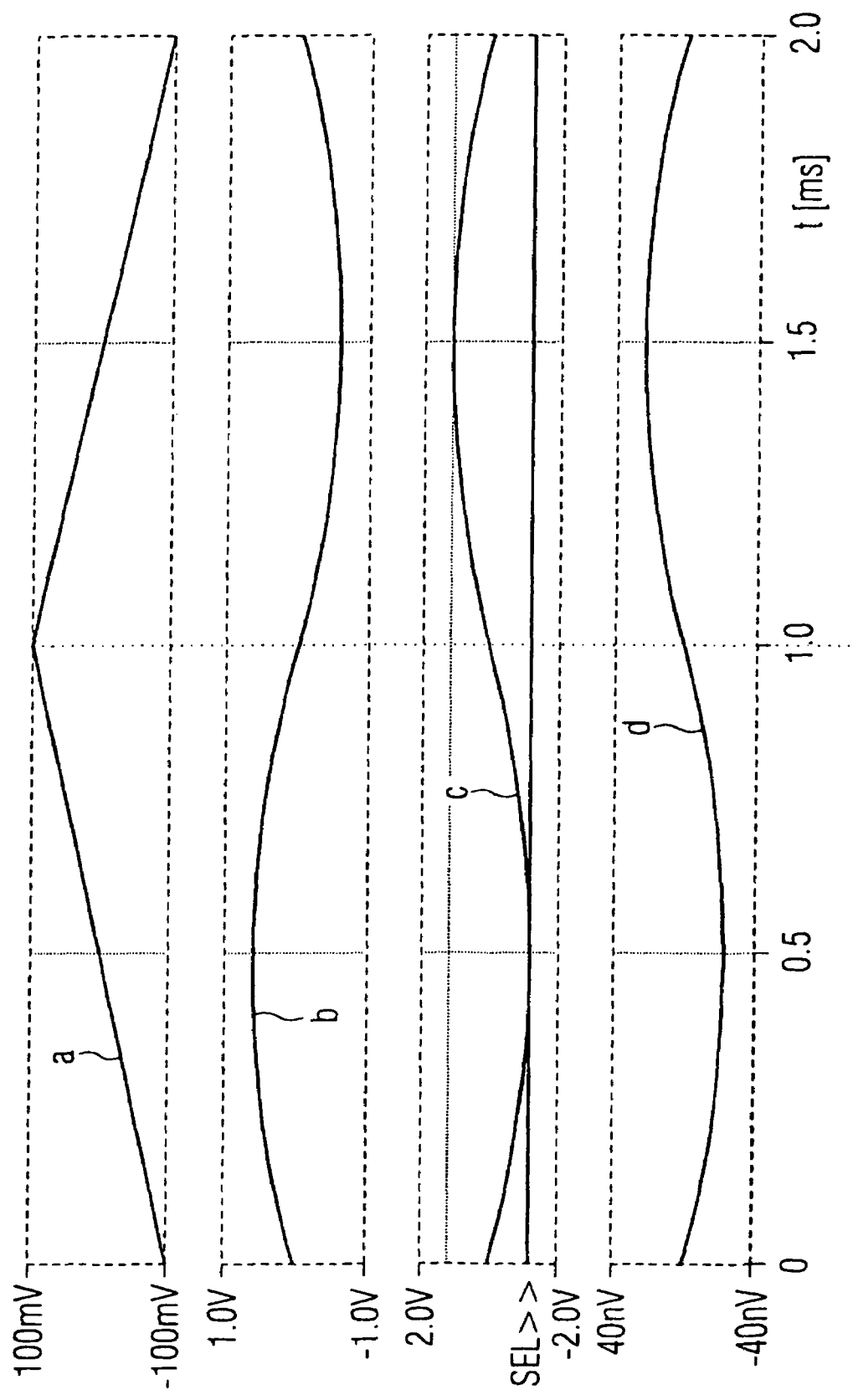

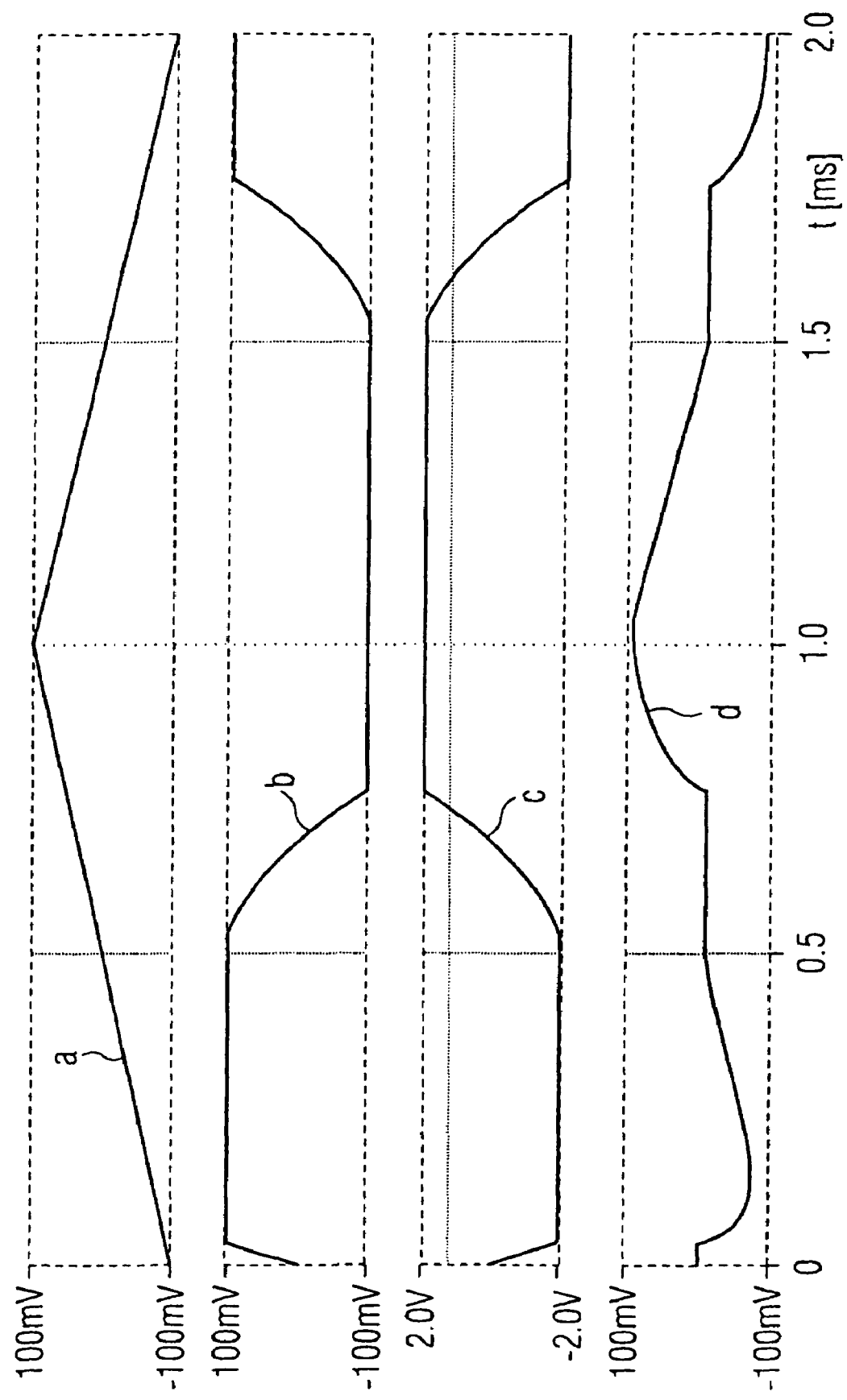

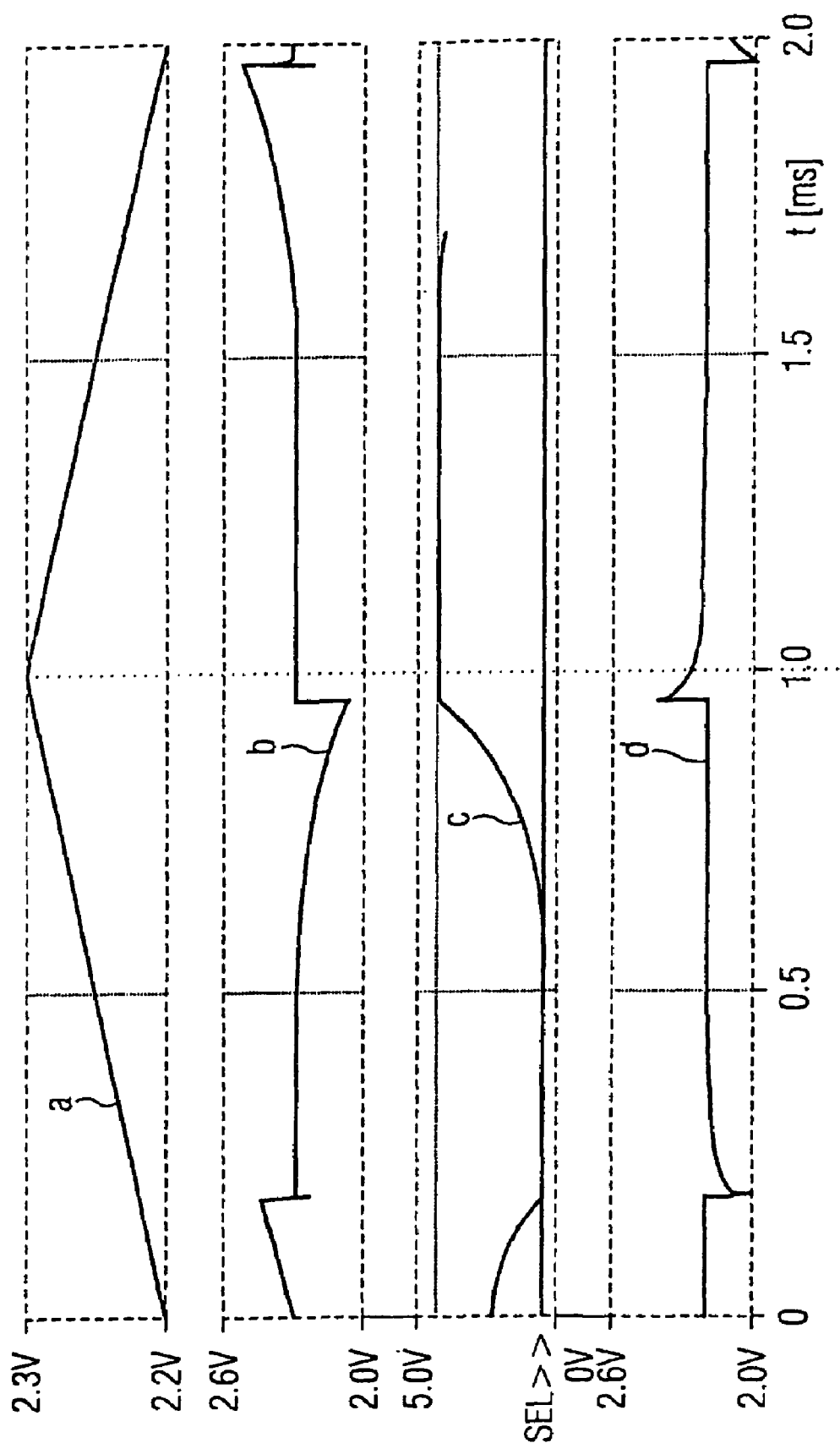

CIRCUIT CONFIGURATION FOR OPERATING A LINEAR EXHAUST-GAS PROBE

CROSS-REFERENCE TO RELATED APPLICATION

This is a continuing application, under 35 U.S.C. § 120, of copending international application No. PCT/DE2003/002822, filed Aug. 22, 2003, which designated the United States; this application also claims the priority, under 35 U.S.C. § 119, of German patent application No. 102 44 466.8, filed Sep. 24, 2002; the prior applications are herewith incorporated by reference in their entirety.

BACKGROUND OF THE INVENTION

Field of the Invention

The invention relates to a circuit configuration for operating a linear exhaust-gas probe of an internal combustion engine. The exhaust-gas probe has a measuring cell for measuring a gas concentration in a measuring chamber of the exhaust-gas probe by determining a measuring-cell voltage, in addition to a pump cell for pumping gas out of the measuring chamber or into the measuring chamber by applying a pump current to the pump cell. The circuit has a comparator circuit for comparing the measuring-cell voltage with a predefined measuring-cell setpoint voltage and for providing an analog deviation signal corresponding to the comparison result, and a pump current source for providing the pump current, the source being controlled by means of the deviation signal using a control circuit for an approximation of the measuring cell voltage to the measuring-cell setpoint voltage.

Recent developments in motor vehicles, with constant reductions in harmful emissions and ever lower fuel consumption, require the internal combustion engine to have a relatively accurate mixture controller. It is an advantage to use for this purpose a so-called linear exhaust-gas probe with pumped reference (measuring cell), since when using such a probe it is possible to achieve relatively accurate measurements of the gas concentration in the exhaust gas (in particular oxygen partial pressure) even when it varies sharply according to the operating status of the internal combustion engine.

In a prior art conventional oxygen probe (lambda probe) a first electrode pair is disposed between a measuring chamber and the ambient air and is used to measure the oxygen concentration in this measuring chamber by measuring a Nernst voltage generated at the test electrodes by the difference in gas concentration. The measuring chamber and the arrangement for the test electrodes together form the afore-mentioned measuring cell. A second electrode pair is disposed between the measuring chamber and the exhaust gas stream, enabling oxygen ions to be pumped into or out of the measuring chamber when an electrical current of the appropriate polarity is applied. For this purpose the measuring chamber communicates with the exhaust gas stream through a diffusion barrier (made of a zirconium ceramic material, for instance). This diffusion barrier and the pump electrodes together form a so-called pump cell.

When that prior art probe is operating, a dynamic equilibrium between diffusion-related and pump-current-related flows of oxygen into and out of the measuring chamber is maintained by means of an appropriate adjustment to the electrical pump current. The oxygen concentration in the measuring chamber determined with the aid of the test electrodes is a suitable control criterion for this purpose. This concentration can be adjusted to a value corresponding to an air/fuel ratio of, say, $\lambda=1$ by way of a Nernst voltage (measuring cell voltage) with a typical value of 450 mV. The pump current flowing through the pump cell in this case is then a measure of the oxygen concentration in the exhaust gas or (after numeric conversion) a measure of the air/fuel ratio of interest.

A circuit configuration by which a linear lambda probe can be operated in this fashion is known, for example, from the commonly assigned German patent DE 101 01 755 C1 and corresponding U.S. patent application publication U.S. 2004/0007045 A1).

In practice, during adjustment of the pump current to achieve a predefined gas concentration in the measuring chamber or obtain a predefined measuring-cell setpoint voltage, the following problem arises: The probe has a defined nominal operating temperature which is typically in the approximate range 500° C. to 800° C. In order to bring the probe up to its operating temperature as soon as possible after starting the internal combustion engine or to purposely adjust the temperature of the probe, a dedicated heating device provided for this purpose is often arranged on the probe. Because the electrical resistance of the ceramic material typically used to provide the diffusion barrier (pump cell) is strongly dependent on temperature, the pump cell is highly resistive during the heating phase. When the pump current is adjusted to achieve a desired gas concentration in the measuring chamber, that is, so that the measuring cell voltage approximates to a predefined measuring-cell setpoint voltage (e.g. 450 mV), the pump voltage which the pump current source applies to the pump cell in order to generate an appropriate pump current is relatively large. Depending on the ceramic material used for the pump cell, if a pump voltage typically around 1.8 V to 2.5 V is exceeded, this can first of all bring about adverse effects in the probe function and may eventually cause irreversible damage to the probe, in particular due to what is known as "blackening" or crazing in the material of the solid electrolyte used in the pump cell.

Two approaches to solving this problem can be found in the prior art.

In the first such approach to a solution the pump cell voltage is permanently limited due to the fact that the pump current source is designed from the outset with an output voltage range which prevents damage to the probe (e.g. +/−2.4 V). In this solution however, the limitation (control range) is rather difficult to change. If the circuit is integrated, the only practical way to do this is to change the supply voltage, which can be disadvantageous for other parts of the circuit. Depending how the pump current source is configured, e.g. by means of an operational amplifier, the limitation value can also be imprecise and dependent on the pump current. When an operational amplifier is used, the limitation value is dependent on the saturation voltage of the onboard output transistors. Moreover in this case transistor recovery times can lead to unwanted transient effects on departing from the limiting status.

In the second such approach to a solution the pump cell voltage is limited by means of a diode connected in parallel to the pump cell. Due to the temperature-dependent characteristic of diodes, such a circuit is strongly dependent on temperature and therefore it too delivers a relatively imprecise limitation. A further serious disadvantage results from the following situation: Depending on the diode characteristic, there is a more or less smooth transition from normal operating mode (without limitation) to a limited mode, i.e. with increasing pump voltage the current by-passed through the limiting diode on the pump cell gradually increases. Since in the limitation mode, part of the current delivered by the pump current source flows through the pump cell and a further part of this current flows through the limiting diode, the current delivered by the pump current source and measured by an analytic circuit is no longer a measure of the current flow through the pump cell and the measurement is falsified.

SUMMARY OF THE INVENTION

It is accordingly an object of the invention to provide a circuit configuration for operating a linear exhaust gas probe which overcomes the above-mentioned disadvantages of the heretofore-known devices and methods of this general type and which reliably limits the pump voltage to a predefined extent and by so doing ensures that the limitation measures taken have the fewest possible adverse effects on the measurement operation.

With the foregoing and other objects in view there is provided, in accordance with the invention, a circuit configuration for operating a linear exhaust-gas probe for an internal combustion engine, wherein the exhaust-gas probe has a measuring cell for measuring a gas concentration in a measuring chamber of the exhaust-gas probe by determining a measuring-cell voltage and a pump cell for pumping gas out of the measuring chamber or into the measuring chamber by applying a pump current to the pump cell. The circuit configuration according to the invention comprises:

a first comparator circuit for comparing the measuring-cell voltage with a predefined measuring-cell setpoint voltage and for providing an analog deviation signal representing a comparison result;

a control circuit;

a pump current source having an output, the pump current source providing the pump current and being controlled by way of the deviation signal via the control circuit for driving the measuring cell voltage to a measuring-cell setpoint voltage;

a second comparator circuit for comparing a voltage applied to the pump cell with at least one predefined threshold voltage and for providing a binary switching signal corresponding to a comparison result; and a switchable counter coupling path between the output of the pump current source and the control circuit of the pump current source, the coupling path being connected when the threshold voltage is exceeded (e.g., when the voltage threshold (+,−) is crossed).

The circuit configuration to which the invention relates is provided with a comparator circuit for comparing the voltage applied to the pump cell with at least one predefined threshold voltage and for providing a binary switching signal corresponding to the comparison result. By using this method the value of a limitation can be determined flexibly and with great accuracy, that is, by means of a predefined threshold voltage with which the pump voltage is compared. The binary switching signal provided as a result of this comparison represents a control signal which can easily be digitally analyzed and which can also be advantageously used by for example an electronic device for controlling the internal combustion engine in order to detect the limitation mode. Furthermore according to the invention a switchable counter coupling path is provided between the output of the pump current source and the control circuit of the pump current source, said path being enabled when the threshold voltage is exceeded (in limitation mode), thereby producing controlled limitation of the pump voltage.

Advantageously the pump voltage can be easily limited to a specified value for adaptation to a particular probe. The voltage limitation can therefore be adjusted precisely and individually. In addition the measurement of the pump current flowing through the pump cell is not falsified by the voltage limitation and said limitation does not interact with the normal operating mode of the circuit configuration. Furthermore the inventive circuit configuration allows limitation to be enabled and disabled without causing instability or any overshoot effects, in that with the aid of the binary switching signal of an engine controller it is a simple matter to indicate the operation of voltage limitation. Measures can be taken to protect the probe in the event of long-duration limitation, for example the probe can be disabled by the engine controller. Lastly the configuration according to the invention avoids the disadvantages of limiting the output voltage of the pump current source itself, and its simple configuration is suitable for integration.

In order to ensure that the pump voltage is limited to a predefined voltage range within which it is permissible for the probe to operate, provision is made, in accordance with an advantageous development of the invention, for the second comparator circuit to be enabled to compare the voltage applied to the pump cell with a predefined first threshold voltage and a predefined second threshold voltage, and enabled also to provide two binary switching signals corresponding to the results of the comparisons. The two threshold voltages define a voltage range which is permissible for the voltage on the pump cell. In the case of the first and second threshold voltages it is possible to envisage for example a positive and a negative threshold voltage if voltages with different polarity may be expected at the output of the pump current source when it is operating. Advantageously these positive and negative voltage limitations can then be predefined individually, in particular with values which differ from one another.

Also at least one of the threshold voltages can be predefined as adjustable and/or switch-selectable, for instance so that the circuit configuration can be individually adapted to different probes.

In a further embodiment of the invention, provision is made for the second comparator circuit to have a comparator for each comparison, and for a first input of said comparator to be connected to the output of the pump current source, and for the corresponding threshold voltage to be applied to a second such input, such that an output of the comparator provides the corresponding binary switching signal and is connected to a control gate of a switching element (such as a switching transistor) which connects the output of the pump current source to an input of the control circuit for the purpose of providing the counter coupling path. This design produces the desired limitation functionality in a way that is particularly suitable for integration. A reference potential of the circuit configuration can be applied to the said control circuit input via a resistor, so that this input or the potential it carries can be used to control the pump current source both in normal operating mode (without counter coupling) and in restricted mode.

Other features which are considered as characteristic for the invention are set forth in the appended claims.

Although the invention is illustrated and described herein as embodied in a circuit configuration for operating a linear exhaust-gas probe, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 6A are signal graphs showing simulated signal variations in the circuit configuration of FIG. 4 in a normal operating mode (FIG. 6a);

FIG. 6B are signal graphs showing simulated signal variations in the circuit configuration of FIG. 4 in an operating mode with pump voltage limitation enabled;

FIG. 8 are signal graphs showing simulated signal variations corresponding to FIG. 6B with pump voltage limitation enabled, but with the circuit configuration of FIG. 7.

DESCRIPTION OF THE PREFERRED EMBODIMENTS

Figure 1:
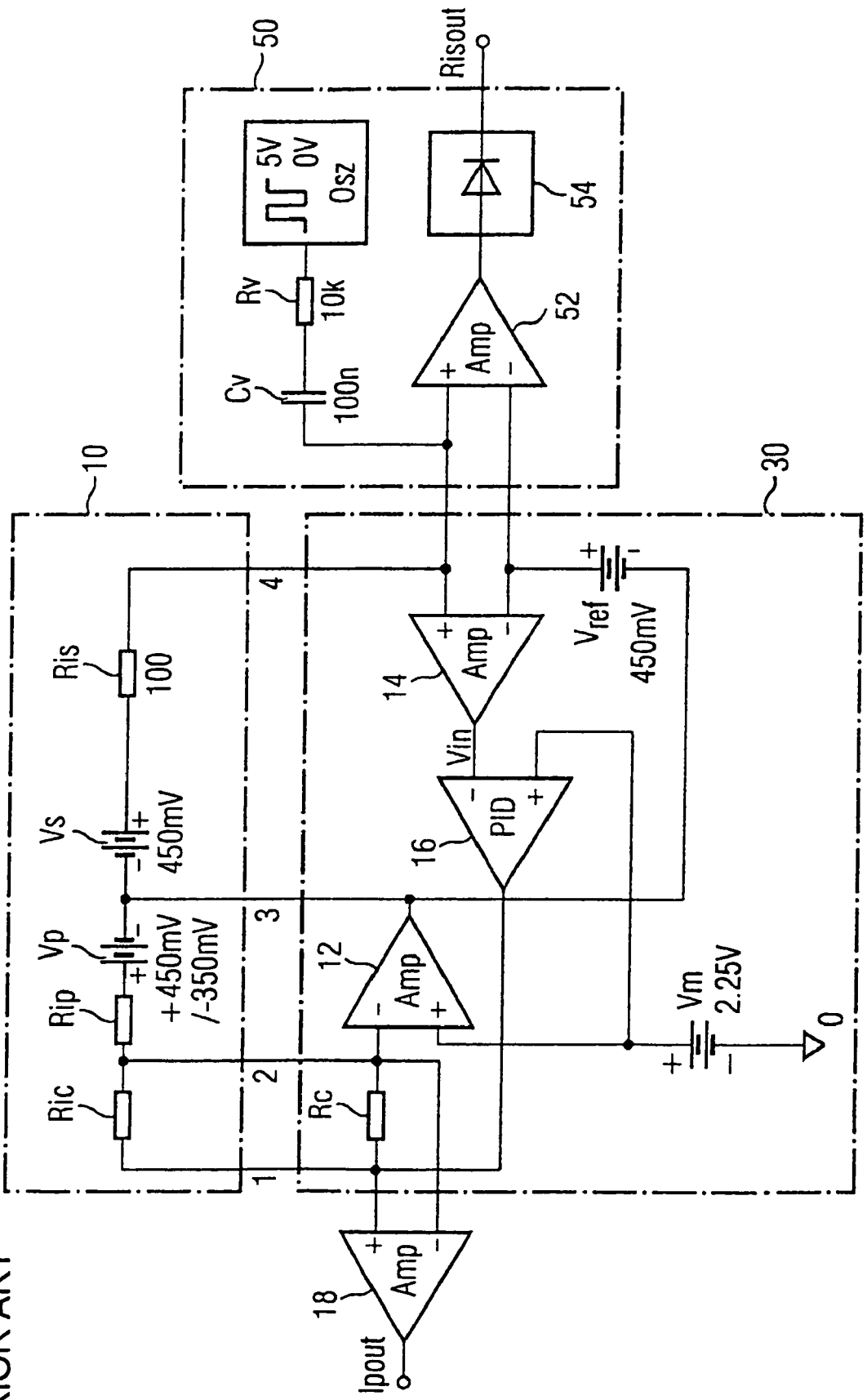
FIG. 1 is a block circuit diagram of a circuit configuration according to the prior art, together with a linear lambda probe which operates with it.

Referring now to the figures of the drawing in detail and first, particularly, to FIG. 1 thereof, there is shown, in the upper part, a conventional probe 10 for measuring the oxygen concentration or the air number λ in the exhaust gas of an internal combustion engine.

The probe 10 comprises a measuring cell represented in the circuit diagram by a Nernst voltage Vs and an internal resistor of the measuring cell Ris, together with a pump cell represented in the circuit diagram by a polarization voltage Vp and an internal resistor of the pump cell Rip. Probe terminals 3 and 4 form a test electrode pair in the probe 10 for measuring the oxygen concentration in a measuring chamber of the probe 10 by determining the measuring-cell voltage Vs between the terminals 3 and 4. It will be understood that the voltage values and component values shown in the figure are intended merely as examples.

When the probe 10 is operating, the oxygen concentration in the measuring chamber is adjusted to a predefined value corresponding to a predefined value of the measuring cell voltage (measuring-cell setpoint voltage) by appropriately controlling a pump current source 12, thereby generating a pump voltage and accordingly a pump current which flows via the terminals 1 or 2 and the terminal 3 through the pump cell and causes a movement of oxygen ions into the measuring chamber or out of the measuring chamber (pumping). The pump current flows via a parallel circuit of a calibration resistor Ric and an external measuring resistor Rc in the probe 10.

The terminal 4 of the probe is connected to the non-inverting input of a differential amplifier 14, to the inverting input of which a measuring-cell setpoint voltage Vref is applied by a voltage source connected between the inverting input and the probe terminal 3. This differential amplifier 14 compares the measuring cell voltage Vs (Nernst voltage) with the measuring-cell setpoint voltage Vref and generates an analog deviation signal Vin at its output. This deviation signal Vin is fed to the inverting input of a PID controller 16, to the non-inverting input of which a mid-range voltage Vm is applied through a voltage source arranged between the said input and a ground connection of the circuit configuration. At the output of the PID-controller 16 a control signal for a subsequent pump current source 12 is formed from the deviation signal Vin. For this purpose the output of the PID-controller 16 is connected via the probe terminal 1 to the calibration resistor Ric of the probe 10 and a terminal of the external measuring resistor Rc, the other terminal of which is connected to the probe terminal 2 as well as to the inverting input of the pump current source 12 configured as an operational amplifier. The non-inverting input of the pump current source 12 is connected to the non-inverting input of the PID-controller 16 and thus also to the mid-range voltage Vm to ground. The PID-controller 16 thus forms a control circuit for the pump current source 12, so that when the probe 10 is operating the measuring cell voltage (Vs) is adjusted in order that it closely approximates to the measuring-cell setpoint voltage (Vref).

The block designated with 30 in the lower part of FIG. 1 forms in summary a regulator for the pump current which is generated in a controlled manner by the pump current source 12 on the basis of a measurement of the measuring cell voltage Vs.

An evaluation amplifier 18 is provided for measuring the pump current flowing through the parallel circuit from Ric, Rc as a measure of the oxygen concentration or air number of the exhaust gas stream. This pump current measurement is performed by measuring the voltage drop in the resistor arrangement Ric, Rc, by connecting the input of this evaluation amplifier 18, formed from a non-inverting input and an inverting input, to these resistors in parallel. The signal Ipout provided at the output of the amplifier 18 is evaluated for mixture preparation and used by an electronic engine controller (e.g. microcontroller—not shown). Because the pump current source 12 is configured as an inverting operational amplifier, the current flowing through the resistors Ric, Rc also flows as pump current through the pump cell of the probe 10, and due to the feedback produced via the pump cell the operational amplifier 12 adjusts its output voltage in such a way that the input voltage difference closely approaches zero. The evaluation amplifier 18 then detects the voltage drop generated by the pump current on the parallel circuit of the resistors Ric and Rc, amplifies this voltage drop and lastly provides a measure of the pump current at its output, in the form of a voltage which is then forwarded to an ADC of the engine controller for further processing.

The block designated 50 in the right-hand part of FIG. 1 represents a prior art circuit for measuring the internal resistor Ris in the measuring cell of the probe 10. Since this internal resistor Ris is greatly influenced by the temperature of the probe 10 and knowledge of the probe temperature is useful for various purposes, this circuit indirectly measures the probe temperature. An AC signal is generated by an oscillator Osz and is modulated via a resistor Rv and a decoupling capacitor Cv of the probe 10, the frequency of the oscillator signal differing sufficiently from the frequency of the useful probe signal. In response to the modulated signal and as a function of the internal resistor Ris of the probe 10, an AC signal is obtained, the amplitude of which is representative of the resistor Ris and thus representative of the probe temperature.

A measure of this amplitude is obtained by amplification of the AC signal with the aid of an amplifier 52 and subsequent rectification by a rectifier 54, at the output of which a signal Risout specifying the probe temperature is provided for the engine controller.

Figure 2:
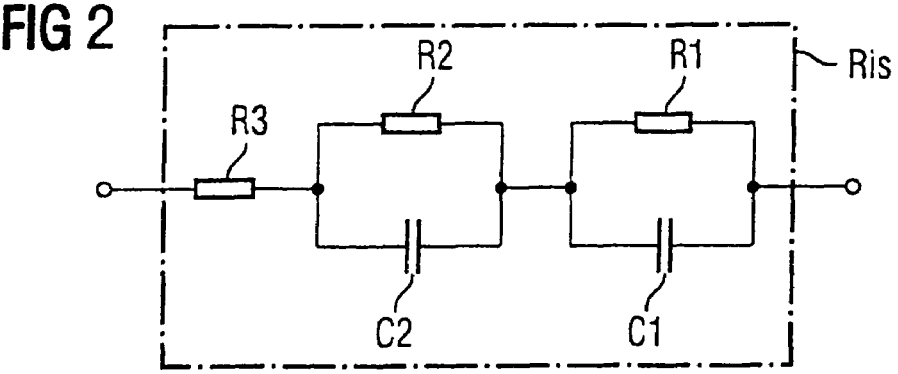
FIG. 2 is a conventional equivalent circuit diagram of the internal resistance in the measuring cell of the prior art lambda probe shown in FIG. 1.

FIG. 2 shows a conventional equivalent circuit diagram of the internal resistor (impedance) Ris of the probe 10. In this diagram R1 and C1 represent the transfer impedance between the electrodes and the ceramic material, R2 and C2 represent the transfer impedance between grain boundaries of ceramic sinter particles and R3 represents the inherent resistance of the sinter ceramic.

Figure 3:
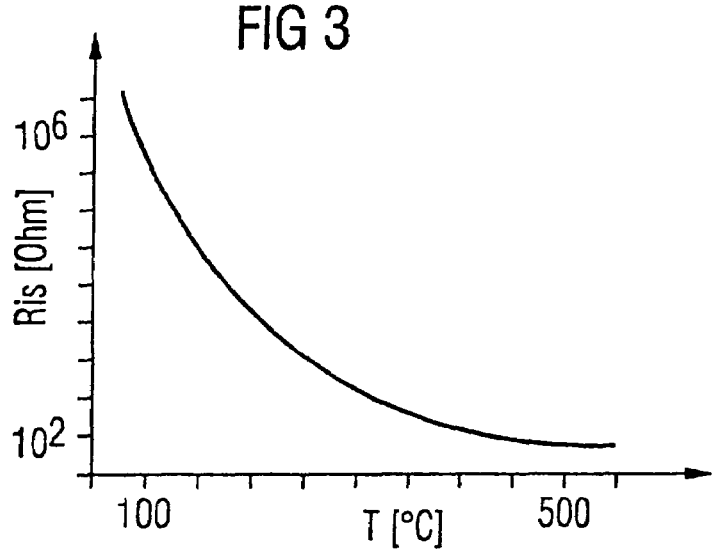
FIG. 3 is a graph illustrating a temperature dependency of the internal resistance.

FIG. 3 shows a semi-logarithmic plot of the strongly temperature dependent internal resistor Ris. From this it is clear that the resistance over the temperature range which is relevant in practice varies by many orders of magnitude. A qualitatively identical characteristic emerges for the internal resistor Rip in the pump cell of the probe 10.

When the circuit shown in FIG. 1 is operating, the following problem arises: The pump cell voltage between the probe terminals 2 and 3 is a function of the polarization voltage Vp (e.g. −350 mV to +450 mV) and the product of the pump current and the pump cell resistance Rip. When the probe is ready to operate, i.e., when the probe 10 has reached its operating temperature of 750° C. for example, the internal resistance Rip amounts to some 100 ohms, so that for a typical pump current of 6 mA the pump cell voltage is approx. 1 V, which is below the pump cell voltages at which damage to the probe 10 due to blackening typically begins.

However, so that the internal combustion engine can be operated in a controlled way as soon as possible after starting, thus contributing to a reduction in emissions, there is a temptation to switch on the probe 10 earlier instead of waiting if possible until the probe 10 has safely reached its normal operating temperature. If the control loop for generating the pump current as described above is then closed during the heating phase of the probe, the differential amplifier 14 will generate a system deviation Vin which the PID-controller 16 converts into a relatively large pump current demand (voltage to Rc, Ric), and the pump current source 12 then attempts to comply with this demand by raising the voltage at the pump cell until the required pump current flows. Even at a probe temperature of 400° C. (corresponding to an internal resistance Rip of 3.5 kilo-ohms kΩ) a pump current requirement of less than 1 mA is enough to exceed typical maximum permissible pump cell voltages. Suitable measures must be taken to avoid this situation, which can permanently damage the probe 10. The measures provided by the invention reliably limit the pump voltage and will be explained below with the aid of exemplary embodiments and by reference to FIG. 4 to FIG. 8.

In the description of exemplary embodiments which follows, the same reference numbers are used for like components or blocks with the addition of a lower case letter to differentiate the embodiment concerned. In the main only the differences relative to exemplary embodiments already described will be mentioned and reference will also be made expressly to the description of previous exemplary embodiments.

Figure 4:
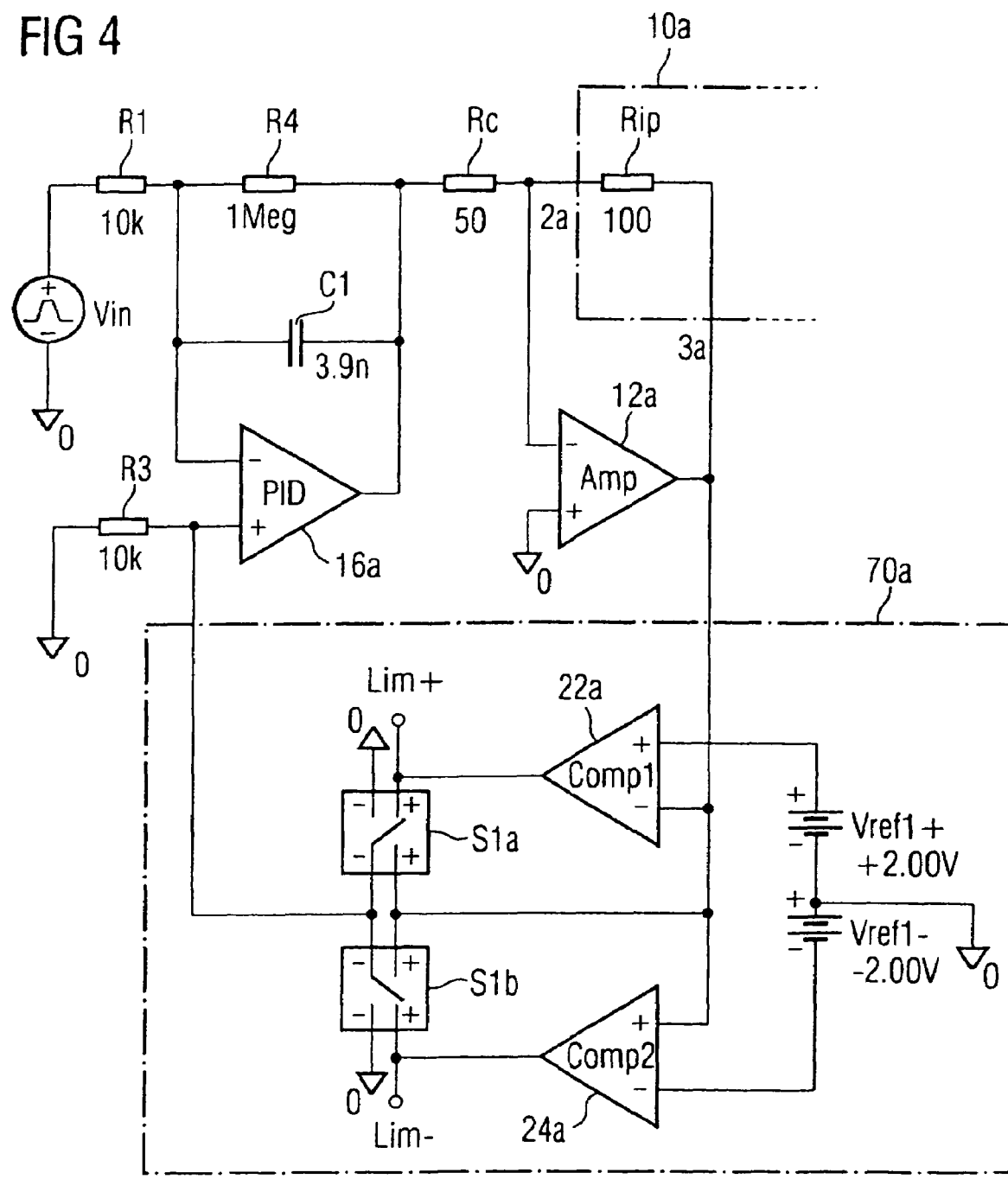
FIG. 4 is a block circuit diagram showing components of a circuit configuration which are of importance to the invention for operating a linear exhaust-gas probe.

FIG. 4 shows a circuit configuration according to the invention for operating a linear lambda probe 10*a*, from which some of the previously explained circuit components that are not important for an understanding of the novel concept have been omitted. Details of their function can be obtained by referring to the explanations about the circuit shown in FIG. 1.

The circuit according to FIG. 4 is configured as follows: A signal source which provides the analog deviation signal Vin already mentioned above is connected to ground on the one hand and to a terminal of a resistor R1 on the other. The other terminal of the resistor R1 leads on to first terminals of a resistor R4 and of a capacitor C1 as well as to the inverting input of a PID-amplifier 16*a*. The non-inverting input of the PID-amplifier 16*a* is connected to the first switching contacts of switching elements S1*a* and S1*b* (e.g. switching transistors) as well as to ground via a resistor R3. The output of the PID-amplifier 16*a* is connected to the second terminals of R4 and C1, as well as via a calibration resistor Rc and a probe terminal 2*a* to an internal resistor Rip in a pump cell of the probe 10*a* and the non-inverting input of an amplifier 12*a* which forms the pump current source. The non-inverting input of the amplifier 12*a* is connected to ground. The output of the amplifier 12*a* leads to the other terminal of the pump-cell internal resistor Rip (probe terminal 3*a*), to the inverting input of a first comparator 22*a*, to the non-inverting input of a second comparator 24*a* and to second switching contacts of the switches S1*a* and S1*b*. The output of the comparator 22*a* is connected to a control input of the switch S1*a*, whereas the output of the comparator 24*a* is connected to a control input of the switch S1*b*. The non-inverting input of the comparator 22*a* is connected to the positive pole of a first threshold voltage source Vref1+, the negative pole of which is connected on the one hand to ground and on the other leads to the positive pole of a second threshold voltage source Vref1−, the negative pole of which is connected to the inverting input of the comparator 24*a*.

The functionality of the circuit is as follows: The components shown in the upper part of FIG. 4, PID 16*a*, R1, R4, C1 and pump current source 12*a* together with Rc and Rip correspond to the typical circuit configuration for adjusting the pump current on the basis of a control deviation signal Vin, as shown in FIG. 1. The signal source shown in FIG. 4 provides this signal Vin and corresponds to the output of the differential amplifier 14 shown in FIG. 1.

The special point to note about the circuit shown in FIG. 4, which is a second comparator circuit 70*a*, is evident from the lower part of the circuit diagram. The voltage at the output of the pump current source 12*a* (pump voltage) is compared by means of the two comparators 22*a*, 24*a* with a positive reference voltage Vref1+ and with a negative reference voltage Vref1−. These two reference voltages define a permissible voltage range for the pump voltage to protect the pump cell from excessively high voltages.

When the pump voltage is present between the positive reference voltage and the negative reference voltage, the outputs of the comparators 22*a*, 24*a* each provide a low-level signal (logic level), which is made available to the non-illustrated engine controller as an indicative signal Lim+ or Lim−.

If, on the other hand, the pump voltage of the pump current source 12*a* exceeds the positive reference voltage Vref1+, the output of the comparator 22*a* changes to a high-level signal, which is indicated to the engine controller via the signal Lim+. The high level of the signal Lim+ causes the switching element S1*a* to close, making a connection between the output of the pump current source 12*a* and the non-inverting input of the PID-amplifier 16*a*. On the other hand, if the pump voltage falls below the negative reference voltage Vref1−, the output of the comparator 24*a* changes to a high-level signal and the switching element S1*b* closes. This situation is also notified to the engine controller via the signal Lim− and by means of the switching element S1*b* causes a connection to be made between the output of the pump current source 12*a* and the PID-amplifier 16*a*.

During normal operation of the circuit configuration, i.e. when the pump voltage is present between the reference voltages Vref1+, Vref1+ acting as threshold voltages, a predefined potential (in this case a ground potential) is applied to the non-inverting input of the PID-amplifier 16a via the resistor R3, whereas if one of the threshold voltages is exceeded due to the closure of the corresponding switching element S1, a counter coupling path is enabled, applying a voltage to the non-inverting input of the PID-amplifier 16a, which, with regard to pump voltage generation, counteracts the demand voltage Vin, so that a stable equilibrium is established between the voltage operating via R1 on the inverting input of the PID-amplifier 16a and the voltage operating via the counter coupling path on the non-inverting input of the PID-amplifier 16a, in such a way that in practice the pump voltage does not exceed the value of a threshold voltage. In summary the output voltage of the pump current source 12a is restricted in a controlled manner to a predefined voltage range (Vref1+, Vref1−).

FIG. 6A and FIG. 6B show this fact with the aid of simulated signal variations for the circuit according to FIG. 4. FIG. 6A shows signals in the normal operating mode (without limitation) and FIG. 6B shows the same signals with limitation. Limitation was simulated by simply increasing the internal resistance Rip of the pump cell from 100 ohms to 1 kilo-ohm and leaving the input signal Vin unchanged.

The reference letters in FIGS. 6A and 6B represent the following:
a: the deviation signal Vin,
b: the signal at the output of the PID-amplifier 16a,
c: the signal at the output of the pump current source 12a,
d: the signal at the non-inverting input of the PID-amplifier 16a.

From FIG. 6A it is evident that starting with the deviation signal Vin provided here as a sawtooth signal, the integrator behavior of the PID-controller 16a converts this signal into a sine signal, which is moreover inverted. The pump voltage (curve c) then always lies within the permissible range defined by the limiting thresholds. The extremely low voltages on the non-inverting input of the PID-amplifier 16a are generated by a finite resistance of the switching elements S1a, S1b and are virtually insignificant.

For the limitation case according to FIG. 6B it is clear that the output signal of the PID-amplifier 16a (curve b) is now drastically limited. Accordingly the output signal of the pump current source 12a (curve c) is exactly on the limiting threshold in the corresponding time periods. Before the limiting threshold is reached the value of the signal at the non-inverting input of the PID-amplifier 16 (curve d) is 0 V. Once the limiting threshold is reached this signal follows the same variation as Vin until the value drops below the limiting threshold again. The signal then drops back to 0 V.

Figure 5:
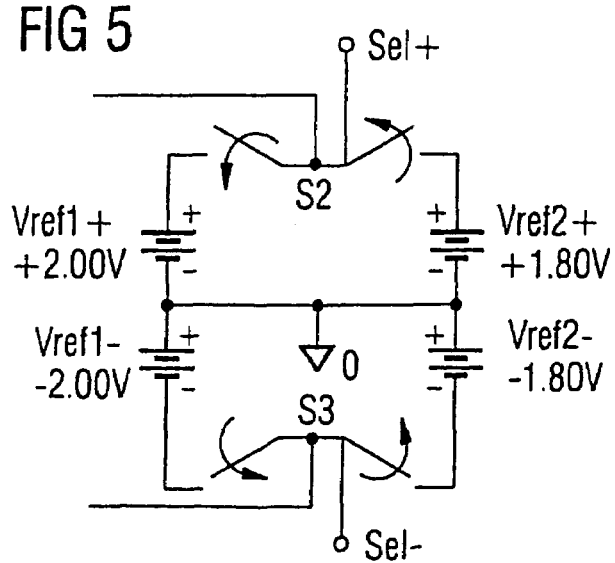
FIG. 5 is a detail from FIG. 4, showing a threshold voltage source in a modified embodiment.

FIG. 5 shows a modification to the circuit configuration according to FIG. 4 in the area of the provision of the threshold voltages. Using this modification it is possible to specify both the positive reference voltage and the negative reference voltage as switch-selectable. For this purpose two positive reference voltages Vref1+, Vref2+ and two negative reference voltages Vref1−, Vref2− are provided. Switching can be carried out with the aid of corresponding control signals Se1+, Se1− using the toggle switches S2 or S3.

Figure 7:
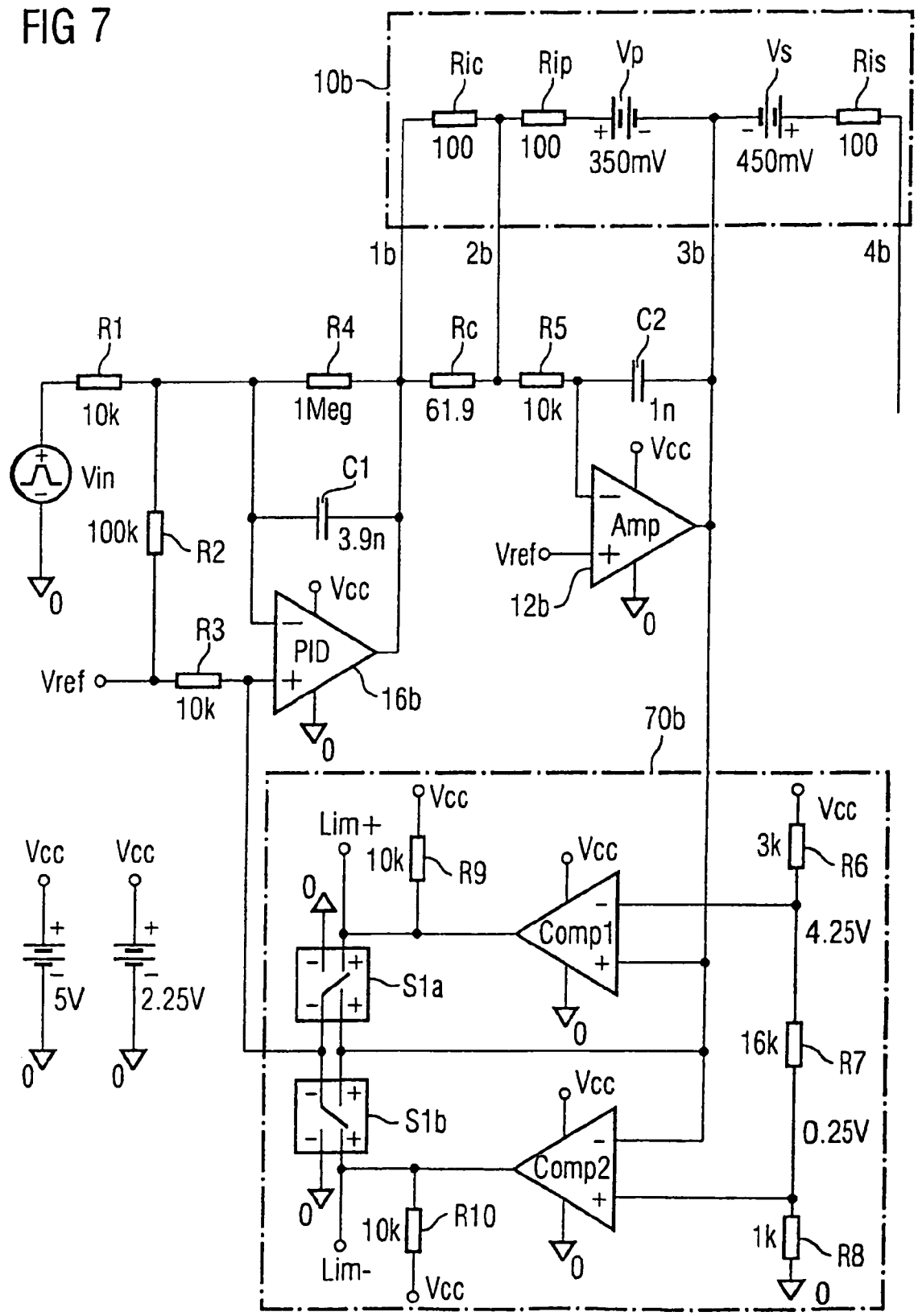
FIG. 7 is a block circuit diagram showing important components in a further embodiment of a circuit configuration according to the invention.

FIG. 7 shows a further embodiment of an inventive circuit configuration, adapted to the application of the known circuit configuration shown in FIG. 1.

Since the supply to the entire circuit shown in FIG. 7 comes from a single voltage source with a positive supply potential Vcc (5V), the non-inverting inputs of the PID-amplifier 16b and of the pump current source 12b are now referenced to a drawn off reference potential Vref (2.25V). Accordingly the threshold voltages of the second comparator circuit 70b have also been altered, namely to a positive reference voltage of 2.25V+2V=4.25V and a negative reference voltage of 2.25V−2V=0.25V. As with the embodiment shown in FIG. 4, here too only a pair of reference voltages is provided for defining the permissible pump voltage range.

The simulated signal variations (similar to FIG. 6B) have also been determined for this circuit configuration in the limitation case and are shown in FIG. 8.

In summary when a predefined threshold is exceeded the invention brings about a limitation of the pump voltage in that the voltage signal that needs to be limited (pump voltage) counteracts the causal control quantity (Vin), or restricts its influence for limitation purposes. In the case of the exemplary embodiments shown, this voltage limitation is produced by means of comparators to which on the one hand the voltage is fed to the output of the pump current source and on the other hand a reference voltage is input, and when this is exceeded subsequent switching elements for enabling a counter coupling path are activated.

I claim:

1. A circuit configuration for operating a linear exhaust-gas probe for an internal combustion engine, the exhaust-gas probe having a measuring cell for measuring a gas concentration in a measuring chamber of the exhaust-gas probe by determining a measuring-cell voltage and a pump cell for pumping gas out of the measuring chamber or into the measuring chamber by applying a pump current to the pump cell, the circuit configuration comprising:
   a first comparator circuit for comparing the measuring-cell voltage with a predefined measuring-cell setpoint voltage and for providing an analog deviation signal representing a comparison result;
   a control circuit;
   a pump current source having an output, said pump current source providing the pump current and being controlled by way of the deviation signal via said control circuit for driving the measuring cell voltage to a measuring-cell setpoint voltage;
   a second comparator circuit for comparing a voltage applied to the pump cell with at least one predefined threshold voltage and for providing a binary switching signal corresponding to a comparison result; and
   a switchable counter coupling path between said output of said pump current source and said control circuit of said pump current source, said coupling path being connected when the threshold voltage is exceeded.

2. The circuit configuration according to claim 1, wherein said second comparator circuit is configured to compare the voltage applied to said pump cell with a predefined first threshold voltage and with a predefined second threshold voltage and to provide two binary switching signals in accordance with the comparisons, and wherein the first and second threshold voltages define a permissible voltage range for the voltage applied to said pump cell.

3. The circuit configuration according to claim 2, wherein at least one of the threshold voltages is an adjustable threshold voltage.

4. The circuit configuration according to claim 3, wherein at least one of the threshold voltages is a switch-selectable threshold voltage.

5. The circuit configuration according to claim 2, wherein at least one of the threshold voltages is an adjustable and switch-selectable threshold voltage.

6. The circuit configuration according to claim 1, wherein said second comparator circuit has a comparator for each comparison, and a first input of said comparator is connected to said output of said pump current source, and a corresponding threshold voltage is applied to a second input, such that an output of said comparator provides the corresponding binary switching signal and is connected to a control gate of a switching element that connects said output of said pump current source to an input of said control circuit for forming said counter coupling path.

* * * * *